US012390226B2

(12) United States Patent
McGuire, Jr.

(10) Patent No.: US 12,390,226 B2
(45) Date of Patent: Aug. 19, 2025

(54) LOW PRESSURE TOURNIQUET WRAP

(71) Applicant: ENTROTECH, INC., Columbus, OH (US)

(72) Inventor: James E. McGuire, Jr., Palm Beach, FL (US)

(73) Assignee: Entrotech, Inc., Columbus, OH (US)

( * ) Notice: Subject to any disclaimer, the term of this patent is extended or adjusted under 35 U.S.C. 154(b) by 144 days.

(21) Appl. No.: 18/007,352

(22) PCT Filed: Jul. 30, 2021

(86) PCT No.: PCT/US2021/043965
§ 371 (c)(1),
(2) Date: Jan. 30, 2023

(87) PCT Pub. No.: WO2022/026869
PCT Pub. Date: Feb. 3, 2022

(65) Prior Publication Data
US 2023/0277195 A1    Sep. 7, 2023

Related U.S. Application Data

(60) Provisional application No. 63/059,092, filed on Jul. 30, 2020.

(51) Int. Cl.
*A61B 17/132* (2006.01)
*A61B 17/00* (2006.01)

(52) U.S. Cl.
CPC ............. *A61B 17/1322* (2013.01); *A61B 2017/00862* (2013.01); *A61B 2017/00951* (2013.01)

(58) Field of Classification Search
CPC ............. A61B 17/132; A61B 17/1322; A61B 2017/00862; A61B 2017/00951; A61B 2017/12004
See application file for complete search history.

(56) References Cited

U.S. PATENT DOCUMENTS

| 2,703,083 A | 3/1955 | Gross |
| 8,591,493 B2 | 11/2013 | McGuire, Jr. |
| 2007/0299467 A1 | 12/2007 | Arias |
| 2010/0059167 A1 | 3/2010 | McGuire, Jr. |
| 2017/0065459 A1 | 3/2017 | Ragg |

FOREIGN PATENT DOCUMENTS

WO    WO2012/070556 A1    5/2012

OTHER PUBLICATIONS

Montgomery et al.; 2019 Recommended Limb Tourniquets in Tactical Combat Casualty Care; Journal of Special Operations Medicine: A Peer Reviewed Journal for SOF Medical Professionals; 19(4); pp. 27-50; Jan. 1, 2019.

*Primary Examiner* — Ryan J. Severson
(74) *Attorney, Agent, or Firm* — Shay Glenn LLP

(57) ABSTRACT

Embodiments of a tourniquet are provided. The tourniquet comprises an elastic layer, an adhesive layer on a first side of the elastic layer and a release layer on a second, opposite side of the elastic layer. The tourniquet can have an elongation of over 100% when 10-25 N per inch of width of tension is applied thereto. The tourniquet can be configured to be applied using a typical amount of tension for applying a bandage (e.g., about 10-20 lbs.) and can provide occlusive pressure to a vessel of a limb.

33 Claims, 1 Drawing Sheet

LOW PRESSURE TOURNIQUET WRAP

CROSS-REFERENCE TO RELATED APPLICATIONS

This application is the U.S. National Stage Entry of International Patent Application No. PCT/US2021/043965, filed Jul. 30, 2021, which claims the benefit of U.S. Provisional Patent Application No. 63/059,092, filed Jul. 30, 2020, the entire disclosure of each is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Tourniquets have been used since World War II to stop blood flow in extremities after an injury. The use of a tourniquet typically involves bounding a material tightly around a wounded body part proximal to the wound. Applying the tourniquet with sufficient compressive force can stop the bleeding and save the wounded from further blood loss. However, traditional mechanically actuated tourniquets are difficult to apply and are often ineffective due to improper application and/or long application times. Accordingly, an improved tourniquet is desired.

SUMMARY OF THE DISCLOSURE

In a first aspect, embodiments of a tourniquet are provided. The tourniquet comprises an elastic layer; an adhesive layer on at least a portion of a first side of the elastic layer; and a release layer on at least a portion of a second side of the elastic layer opposite from the first side thereof, wherein the tourniquet has an elongation of over 100% when 10-25N per inch of width of tension is applied thereto.

In some embodiments, the elastic layer comprises polyurethane.

The adhesive layer can comprise a pressure sensitive adhesive. In some embodiments, the adhesive layer comprises an acrylic pressure sensitive adhesive layer. The adhesive layer can be configured to retain its tack when exposed to exudates and other moisture. In some embodiments, the adhesive layer comprises (meth)acrylate. The adhesive layer can comprise a non-sensitizing acrylic. In some embodiments, the adhesive layer is configured to be releasable from the release layer when unwound or peeled and to remain adhered to the release layer when shear is applied thereto.

The tourniquet can be provided in a cube form. The tourniquet can be provided in a roll form.

In some embodiments, the tourniquet is opaque.

The tourniquet can comprise a print copy layer.

In some embodiments, the tourniquet is configured to provide over 100 mmHg of pressure when wrapped circumferentially around a limb a plurality of times. The plurality can be at least 3 times. In some embodiments, the tourniquet is configured to provide 140-160 mmHg of pressure when wrapped circumferentially around a limb a plurality of times. The plurality can be at least 3 times.

In some embodiments, the tourniquet has an elongation of 110-140% when 10-25 N per inch of width of tension is applied thereto. In some embodiments, the tourniquet has an elongation of over 100% when 15-18.75N per inch of width of tension is applied thereto.

In some embodiments, a force required for 100% elongation of the tourniquet is about 70 oz. per inch of width. In some embodiments, a force required for 100% elongation of the tourniquet is about 60-80 oz. per inch of width. In some embodiments, a force required for 100% elongation of the tourniquet is about 40-100 oz. per inch of width. In some embodiments, a force required for 100% elongation of the tourniquet is about 40 oz. per inch of width. In some embodiments, a force required for 100% elongation of the tourniquet is about 34-46 oz. per inch of width. In some embodiments, a force required for 100% elongation of the tourniquet is about 20-35 oz. per inch of width.

The tourniquet can be configured to reach 100% elongation upon application of less than about 10 pounds. In some embodiments, the tourniquet is configured to reach 100% elongation upon application of less than about 20 pounds. The tourniquet can be configured to reach 100% elongation at less than about 10-20 pounds.

In some embodiments, the elastic layer comprises an extensible material imparting recovery of at least 90% when stretched to at least 100% of its length. The elastic layer can comprise an extensible material imparting recovery of at least 75% when stretched to at least 100% of its length. In some embodiments, the elastic layer comprises an extensible material imparting recovery of at least 50% when stretched to at least 100% of its length. The elastic layer can comprise an extensible material imparting recovery of at least 10% when stretched to at least 100% of its length.

The tourniquet can exhibit less than about 3% deformation when stretched to 25% of its length. The tourniquet can exhibit less than about 8% deformation when stretched to 50% of its length.

In some embodiments, the elastic layer comprises an extensible material imparting recovery of at least 90% when stretched to at least 100% of its length.

The tourniquet can be configured to provide pressure sufficient to cause vessel occlusion when wrapped circumferentially around a limb a plurality of times without use of mechanical actuation or a locking mechanism.

In some embodiments, the elastic layer has a width of about 4 inches. The elastic layer can have a width of about 2-6 inches.

In some embodiments, the tourniquet is configured to apply pressure sufficient to occlude a vessel when providing about 100-200 mm Hg. The tourniquet can be configured to apply pressure sufficient to occlude a vessel when providing less than about 200 mm Hg.

In another aspect, embodiments of a method for providing vessel occlusion to a patient is provided. The method comprises stretching a tourniquet comprising an elastic layer, an adhesive layer on a first side of the elastic layer, and a release layer on second side of the elastic layer, opposite the adhesive layer; and wrapping the tourniquet around a limb of the patient a plurality of times, thereby occluding flow in the vessel.

In some embodiments, wrapping the tourniquet around the limb comprises aligning the tourniquet with an underlying layer.

Wrapping the tourniquet around the limb can comprise adhesively securing the tourniquet to an underlying layer. In some embodiments, the tourniquet is under tension while adhesively securing the tourniquet to an underlying layer.

The tension can be less than 25N per inch of width. The tension can be less than 10-25N per inch of width. The tension can be 15-25N per inch of width.

The method can comprise stretching the tourniquet while adhesively securing the tourniquet to an underlying layer. In some embodiments, stretching the tourniquet comprises stretching the tourniquet to greater than 25% of its length. In some embodiments, stretching the tourniquet comprises stretching the tourniquet to greater than 50% of its length. In some embodiments, stretching the tourniquet comprises stretching the tourniquet to greater than 75% of its length. In some embodiments, stretching the tourniquet comprises stretching the tourniquet to greater than 100% of its length.

The tourniquet can be configured to elastically recover after being stretched.

Stretching the tourniquet can comprise applying less than 25 N per inch of tension to the tourniquet. In some embodiments, stretching the tourniquet comprises applying 10-25 N per inch of tension to the tourniquet. In some embodiments, stretching the tourniquet comprises applying 15-18.75 N per inch of tension to the tourniquet.

Stretching the tourniquet can result in elongation of at least about 100%.

The plurality of times can be at least 3 times.

In some embodiments, wrapping the tourniquet comprises providing at least 100 mm Hg occlusive pressure to the limb. In some embodiments, wrapping the tourniquet comprises providing at least 140-160 mm Hg occlusive pressure to the limb. In some embodiments, wrapping the tourniquet comprises providing about 180-500 mm Hg occlusive pressure to the limb.

In some embodiments, wrapping the tourniquet comprises providing about 100-200 mm Hg occlusive pressure to the limb, thereby occluding blood flow in a vessel of the limb. In some embodiments, wrapping the tourniquet comprises providing less than about 200 mm Hg occlusive pressure to the limb, thereby occluding blood flow in a vessel of the limb.

In yet another aspect, embodiments of a tourniquet is provided. The tourniquet comprises an elastic layer; an adhesive layer on at least a portion of a first side of the elastic layer; and a release layer on at least a portion of a second side of the elastic layer opposite from the first side thereof, wherein the tourniquet has an elongation of over 100% when 10-25 N per inch of width of tension is applied thereto, and wherein the tourniquet has a recovery of greater than 90% when stretched to at least 100% elongation.

In a further aspect, embodiments of a tourniquet is provided. The tourniquet comprises an elastic layer; an adhesive layer on at least a portion of a first side of the elastic layer; and a release layer on at least a portion of a second side of the elastic layer opposite from the first side thereof, wherein the tourniquet is configured to provide sufficient pressure to occlude a vessel in a limb of a patient with a mean tourniquet pressure of about 100-200 mm Hg.

In still another aspect, embodiments of a method for providing vessel occlusion are provided. The method comprises stretching a tourniquet comprising an elastic layer, an adhesive layer on a first side of the elastic layer, and a release layer on second side of the elastic layer, opposite the adhesive layer; and wrapping the tourniquet around a limb of the patient a plurality of times such that the pressure applied by the tourniquet is about 100-200 mm Hg, thereby occluding flow in the vessel.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
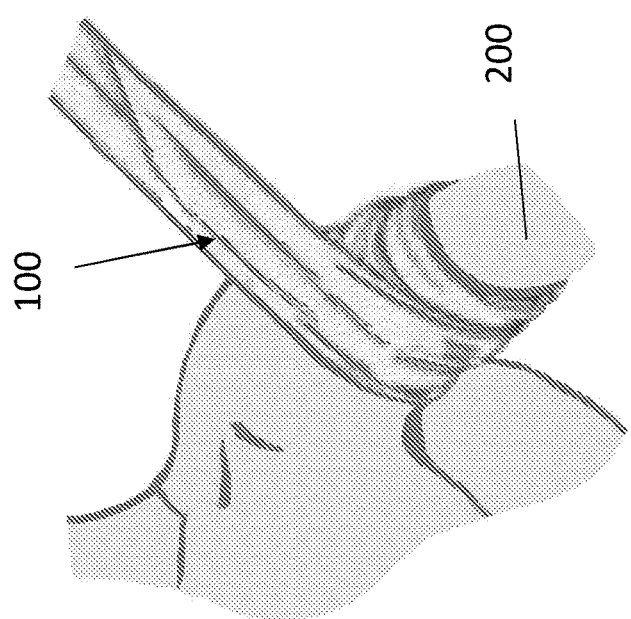
FIG. 1 shows application of a tourniquet to a limb.

Described herein is a tourniquet designed to apply compression without the use of a mechanical actuation mechanism (e.g., without the use of a buckling or winding mechanism). The tourniquet can be a multi-layer thin film. The tourniquet can have an adhesive along the inner surface so as to adhere to the user's skin and/or to the tourniquet itself. Referring to FIG. 1, the tourniquet 100 can be configured to stretch upon application of axial tension. While still under tension, the tourniquet can be wrapped multiple times (e.g., 3-5 times) circumferentially around a limb 200 to enable sufficient compression to reduce and/or stop blood flow. The tourniquet can be configured to be applied using the typical amount of force used to apply bandages (e.g., about 10-20 lbs.).

There are currently a number of windlass-based tourniquets commercially available. The nontraditional adhesive-based tourniquets, such as those described herein, have been found to be equivalent to the windlass-based tourniquets in terms of effectiveness of occlusion and time to occlusion. It has recently also been discovered that a nontraditional adhesive-based tourniquet such as those described herein are able to achieve arterial occlusion using about 40% less pressure than that used by a traditional windlass-based tourniquet (e.g., about 108 mm Hg, about 100-120 mm Hg, about 90-130 mm Hg, etc.). Importantly, while the nontraditional adhesive-based tourniquet is capable of achieving mean tourniquet pressures in the range of 180-500 mm Hg, these high pressures were not necessary to achieve the desired result of arterial occlusion. For example, the adhesive-based tourniquet may achieve vessel occlusion at a mean tourniquet pressure of about 100-200 mm Hg, while other tourniquet types may require mean tourniquet pressures of about 200-350 mm Hg for the same injury type. Achieving arterial occlusion at a lower pressure significantly reduces a leading risk factor for tourniquet-associated limb injury. Additionally, a nontraditional adhesive-based tourniquet such as those described herein has the additional advantage of being smaller and lighter than windlass-based devices.

Figure 2:
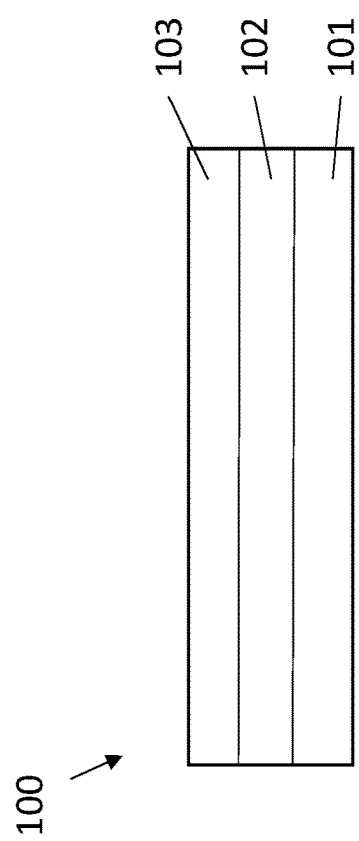
FIG. 2 is a cross-section of a tourniquet.

Referring to FIG. 2, an exemplary tourniquet 100 can include a plurality of layers. The innermost layer can be an adhesive layer 101, the middle layer can be an elastic layer 102, and the outermost layer can be a release layer 103.

The elastic layer 102 can include any suitable material to provide desired properties in tourniquets. The elastic layer 102 can function as a backing or intermediate substrate of the tourniquet, with the adhesive layer 101 and the release layer 103 disposed on opposite sides thereof.

Exemplary materials for use in the elastic layer 102 include, for example, polyvinyl chloride, polyvinyl acetate, polypropylene, polyester, poly(meth)acrylate, polyethylene, polyurethane, and rubbery resins (e.g., silicone elastomers). In some embodiments, the elastic layer can comprise an elastomer with an elongation to failure of greater than 225% (e.g., polyurethane, rubbery resins, etc.).

In some embodiments, the tourniquet 100 can be transparent or translucent to facilitate viewing of the skin thereunder during and after its application thereon. In other embodiments, the tourniquet 100 can be opaque, colored, camouflaged, or black. Thus, according to one embodiment, the elastic layer 102 can include a relatively clear, UV-stable resin such as, for example, a silicone. According to another embodiment, the elastic layer 102 can be polyurethane-based.

In some embodiments, the elastic layer 102 includes polyol, a catalyst, a UV stabilizer, and isocyanate. The components of a specific exemplary embodiment of an elastic layer 102 are shown below in Table 1.

TABLE 1

| Weight % | Material | Description | Supplier |
|---|---|---|---|
| 46.8% | ECA-392 | Mid MW Polyol | entrochem |
| 7.0% | ECA-459 | Mid MW Polyol | entrochem |
| 5.3% | ECA-386 | Low MW Polyol | entrochem |
| 0.0050% | ECA-388 | Catalyst | entrochem |
| 0.5% | ECA-460 | UV stabilizer | entrochem |
| 40.4% | ECA-387 | Isocyanate | entrochem |

A primary advantage the elastic layer 102 is the extensibility and recovery they impart to the tourniquet. The extensibility can allow the tourniquet to be easily stretched during application and to be held in the stretched position as it is circumferentially applied around the limb. The stretched layer, upon being wrapped circumferentially around the limb, is adhesively secured under tension thus providing occlusive pressure. The tension within the layer is proportional to the degree of stretch imparted to the layer. The occlusive pressure provided is proportional to the tension maintained in that layer.

The terms "extensible" and "extensibility" refer to a material's ability to be stretched and recover to essentially its original state after stretching (e.g., in contrast to plastically deforming). For example, such extensibility is evident when elongating (also referred to as stretching) the material by at least about 25%. In one embodiment, the elastic layer 102 comprises an extensible material imparting recovery (i.e., initial length of the sample divided by length of the relaxed sample) of greater than 90% when a sample of such is stretched 25%, 50%, 100%, or 150% of its initial length according to ASTM D412. In another embodiment, the elastic layer 102 comprises an extensible material imparting recovery of at least about 95% when tested as such. In yet a further embodiment, the elastic layer 102 comprises an extensible material imparting recovery of at least about 99% when so tested. In still a further embodiment, the elastic layer 102 comprises an extensible material imparting about 100% recovery when so tested. Such recovery was found to facilitate continued adherence of tourniquets on or near wounds and adequate blood vessel occlusion, according to the invention. Although many conventional tourniquets may provide adequate compression when initially applied, the tourniquet can fail to provide adequate blood vessel occlusion over time (e.g., when the tourniquet shifts or when the limb diameter reduces due to loss of blood). In contrast, the tourniquets described herein actively adjust to changing limb circumference and are capable of maintaining constant positive pressure for blood vessel occlusion due to the high degree of stretch imparted during application and their enhanced ability to recover after elongation. Advantageously, this constant pressure is possible without the need to readjust the tourniquet or apply further compression after initial application of the tourniquet.

In some embodiments, elastic layer 102 is substantially impervious to moisture (i.e., non-porous).

The elastic layer 102 can include any suitable additives. Additives can be selected as known to those skilled in the art based on the intended application. Those skilled in the art are readily able to determine the amount of such additives to use for the desired effect. For example, while the use of certain amounts of crosslinker may still allow formation of suitable tourniquets as described herein, if crosslinkers are present in the elastic layer, they are generally used in an amount of less than about 4 parts by weight, and preferably less than about 2 parts by weight, based on 100 parts by weight of any polymer crosslinkable therewith prior to any crosslinking reaction. Further, crosslinkers may be present if they are not used in combination with polymers that are crosslinkable therewith or where, if crosslinkable, resulting crosslink density is minimal (e.g., due to minimal reactive sites on the base polymer) so as not to significantly affect extensibility of the tourniquet. In a preferred embodiment, the elastic layer is essentially free of crosslinkers and reaction products thereof. As such, crosslinkers and reaction products are generally not discernible therein when using chemical analysis.

Dimensions of the elastic layer 102 can be selected according to the desired application. According to exemplary embodiments, thickness of the elastic layer 102 is about 50 microns (2 mils) to about 250 microns (10 mils), preferably about 75 microns (3 mils).

In some embodiments, the elastic layer 102 has a width of about 15 centimeters (six inches). This significant width was found to facilitate occlusion without applying high pressures that can cause nerve injury etc. In another embodiment, the elastic layer has a width of about 5 centimeters (two inches) to about 10 centimeters (four inches). The elastic layer has a width of about 10 centimeters (four inches) in a preferred embodiment.

The adhesive layer 101 can be configured to adhere the tourniquet to itself (i.e., the adhesive layer 101 can adhere to the release layer 103) as it is wrapped around the patient, e.g., a limb. The adhesive layer 101 can include any suitable material to provide desired properties in the tourniquet 100. If desired to remove at least a portion of the tourniquet 100, temporarily or permanently, it is capable of being easily peeled back from itself. Further, after being so removed, the tourniquet 100 can be capable of effectively re-adhering in preferred embodiments. In some embodiments, the adhesive layer 101 includes a pressure-sensitive adhesive.

In some embodiments, the tourniquet 100 described herein is constructed such that the adhesive layer 101 effectively retains its tack when exposed to exudates and other moisture, obviating the need to utilize an absorbent layer to prevent slippage or unwanted shedding of the tourniquet due to contact with excess exudates. As such, environmental conditions in which the tourniquet 100 can be effectively utilized are expanded.

According to one embodiment, the adhesive layer 101 can include a base polymer with one or more additives such as that described in U.S. Patent Publication No. US-2010-0059167-A1, incorporated herein by reference in its entirety. In one embodiment, the base polymer in the adhesive layer 101 can be (meth)acrylate (i.e., acrylate and methacrylate). In particular, an adhesive based on 2-ethyl hexyl acrylate, vinyl acetate, and acrylic acid monomers polymerized as known to those skilled in the art can be used as the base polymer. However, other suitable chemistries are known to those skilled in the art and include, for example, those based on synthetic and natural rubbers, polybutadiene and copolymers thereof, polyisoprene and copolymers thereof, and silicones (e.g., polydimethylsiloxane and polymethylphenylsiloxane).

Suitable additives can optionally be used in conjunction with the base polymer in the adhesive layer 101. For example, stabilizers (e.g., antioxidants, heat stabilizers, and UV-stabilizers), crosslinkers (e.g., aluminum or melamine crosslinkers), corrosion inhibitors, tackifiers, plasticizers, photocrosslinkers, colorants, fillers, and other conventional adhesive additives as known to those of ordinary skill in the art can be incorporated into the adhesive layer 101. If desired, an adhesion promoter may be included in the adhesive layer 101. However, in preferred embodiments, the material comprising the adhesive layer 101 is selected to be chemically compatible with the elastic layer 102. Thus, an adhesion promoter is not required according to some embodiments.

The adhesive layer 101 can be essentially free of components that may tend to migrate to its interface with the elastic layer, where such components may promote interlayer delamination. In an exemplary embodiment, the adhesive layer has less than about 0.1% residual monomer.

In a further exemplary embodiment, the adhesive layer 101 can include a non-sensitizing acrylic (i.e., as determined when tested in vitro based on the "International Organization for Standardization: Biological Evaluation of Medical Devices, Part 5: Test for Cytotoxicity in vitro Method" (ISO 10993-5) such as, for example, by overlaying confluent monolayers of L-929 mouse fibroblast cells with adhesive samples, incubating the same in 5% carbon dioxide for twenty-four hours at 37° C., and then examining the resulting cell cultures to determine the zone of cell lysis, if any). An exemplary adhesive comprises ECA 134, a solution acrylic pressure-sensitive adhesive available from Entrochem, Inc. (Columbus, Ohio). Another example comprises Entrotape 947A, a white pigmented solution acrylic pressure sensitive adhesive film available from Entrotech, Inc.

Dimensions of the adhesive layer 101 can be selected according to the desired application. According to exemplary embodiments, thickness of the adhesive layer is about 2.5 microns (0.1 mil) to about 150 microns (6 mils), preferably about 50 microns (2 mils) or 75 microns (3 mils).

The adhesive layer 101 may be continuous or discontinuous. According to an exemplary embodiment, width of the adhesive layer 101 approximates width of the elastic layer. As such, in one exemplary embodiment, the adhesive layer 101 has a width of about 15 centimeters (six inches) and, in another exemplary embodiment, the adhesive layer has a width of about 5 centimeters (two inches) to about 10 centimeters (four inches).

The release layer 103 can be configured to enable unwinding of the tourniquet 100. The release layer 103 can thus be non-stick when unwound or peeled, but can adhere to the adhesive layer 101 when shear is applied thereto (thereby ensuring that the tourniquet 100 remains adhered after being wrapped around the limb of the patient unless purposefully lifted away). Further, the release layer 103 can include any suitable material and dimensions. A release layer 103 can comprise, for example, materials conventionally used in the low adhesion backside of a tape. In some embodiments, additional low surface energy materials can be used for enhanced release properties. While not conventionally used in such applications, materials providing premium easy release properties can be used in some embodiments to decrease and often effectively eliminate noise generated when unwinding the tourniquet 100. Importantly, minimization or elimination of unwind noise facilitates stealth when using the tourniquet 100 on, for example, a battlefield. Stealth is often critical in order to avoid undesired alerting of others to the wounded's location when applying a tourniquet to the wounded. In one embodiment, unwind noise is essentially non-existent upon unwind of a roll or cube of the tourniquet 100. In an exemplary embodiment, when a two-inch wide release-coated sample is peel tested at an unwind speed of about 7.7 meters/minute (300 inches/minute) and 90° angle, a release force of less than about 100 grams is measured, and no audible noise is observed when using such a premium easy release material.

In one embodiment, the release layer 103 is silicone-based. In some embodiments, such materials comprise those solventless, platinum-catalyzed vinyl silicone release materials available from Dow Corning Corporation under the SYL-OFF trade designation. One specific example of a release layer 103 is SYL-OFF 7680-010 silicone polymer available from Dow Corning Corporation.

Dimensions of the release layer 103 can be selected according to the desired application. According to some embodiments, thickness of the release layer is about 0.01 micron to about 5 microns, preferably about 4 microns.

The release layer 103 may be continuous or discontinuous. According to an exemplary embodiment, width of the release layer approximates width of the elastic layer 102. As such, in one exemplary embodiment, the release layer 101 has a width of about 15 centimeters (six inches) and, in another exemplary embodiment, the release layer has a width of about 5 centimeters (two inches) to about 10 centimeters (four inches).

It will be appreciated that, in some embodiments, while the layers are described as separate, a single product may provide multiple layers of the tourniquet 100. For example, in some embodiments, as described above, the elastic layer 102 comprises HammerThane® 1973, available from Entrotech, Inc. This product comprises a release layer.

Figure 3:
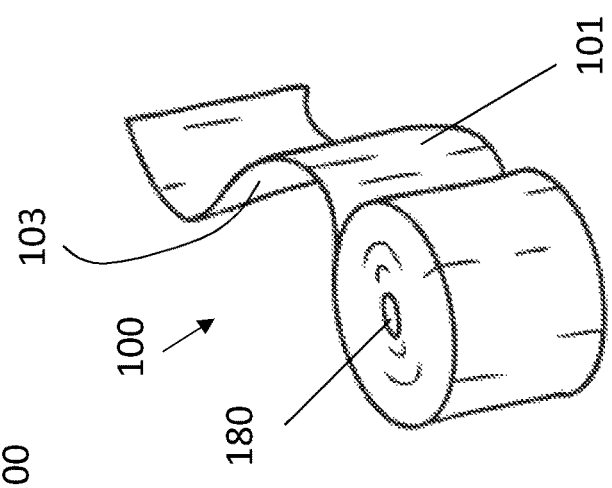
FIG. 3 shows a tourniquet in rolled form.

Referring to FIG. 3, in some embodiments, the tourniquet 100 can be provided in a cube or roll form (e.g., as a tape). As illustrated therein, the tourniquet 100 can include the adhesive layer 102 on a first side (of an elastic layer 102) and the release layer 103 on an opposite second side. A core 180 may optionally be present when providing the tourniquet 100 in roll form. When present, the core 180 can have any suitable dimensions. In an exemplary embodiment, a core 180 having an outer diameter of one inch or less, such as less than ½ inch, such as approximately ¼ inch, which can advantageously minimize the overall volume of the tourniquet. Advantageously, a core having these dimensions can still be easy for the user to handle during use. When provided in a cube or roll form, a pull-tab or similar mechanism may also optionally be provided for easily unwinding the tourniquet at the start of a roll as known to those of ordinary skill in the art.

Advantageously, as discussed above, an important consideration is size and weight of the tourniquet that must often be transported along with other essential provisions on a combat soldier. The tourniquets described herein advantageously have a much smaller size and weight than traditionally available tourniquets.

Referring back to FIG. 1, the tourniquet 100 described herein can advantageously stretch or elongate upon an application of longitudinal force (i.e., tension) while wrapping the tourniquet 100 around the limb 200 (e.g., when wrapping 3-5 times around the limb).

Thus, during use, the user can create tension in the tourniquet 100 by stretching it elastically. Wrapping this elastically-stretched (tensioned) tourniquet 100 circumferentially around the limb 200 and adhesively securing it to itself in an overlapping fashion generates circumferential pressure (i.e., compression) on the underlying tissue of the limb 200.

Overlapping layers (or wrappings) of the tourniquet 100 progressively increase tension in the applied tourniquet 100, resulting in proportionately higher circumferential pressures on the limb 200. In some embodiments, the number of wrappings can be 3-5 for vessel occlusion. In some embodiments, a force of 40-100N, such as 50-80N, such as 60-75N can be applied to the tourniquet 100, which can result in an elongation over 100%, such as 105-150%, such as 110-140%, such as 115%-135% elongation. The elongation of the tourniquet 100 by over 100% can result in a circumferential pressure on the limb or wound over 90 mmHg, such as 100 mmHg or more, such as 100-200 mmHg, such as 120-180 mmHg, such as 140-160 mmHg, such as approximately 150 mmHg of pressure on the wound to provide vessel occlusion.

In some embodiments, the force required for 100% elongation of the tourniquet 100 described herein is about 70 oz. per inch of width (e.g., 280 oz. for a 4-inch wide tourniquet 100). In some embodiments, the force required for 100% elongation of the tourniquet is about 60-80 oz. per inch of width (or 240-320 oz. for a 4-inch wide tourniquet). In some embodiments, the force required for 100% elongation is about 40-100 oz. per inch of width (e.g., 160-400 oz. for a 4-inch wide tourniquet). For example, in some embodiments, the tourniquet can reach 100% elongation using 40 oz. per inch of width (e.g., 160 oz. of force for a 4-inch wide tourniquet). In some embodiments, the tourniquet can reach 100% elongation using about 34-46 oz. per inch of width (or 136-184 oz. of force for a 4-inch wide tourniquet).

According to other embodiments, the tourniquet 100 exhibits greater than about 225% elongation at break when tested according to ASTM D412. In some embodiments, the tourniquet 100 exhibit greater than about 250% elongation at break when tested as such. In some embodiments, the tourniquet 100 exhibits greater than about 300% elongation at break when tested as such. In still further embodiments, the tourniquet 100 described herein exhibit greater than about 350% elongation at break when tested as such.

In some embodiments, the tourniquet 100 exhibits essentially no plastic deformation when stretched according to ASTM D412 up to about 150% of their initial length. According to some embodiments, the tourniquet 100 exhibits less than about 3% deformation after 25% elongation when tested according to ASTM D412. In some embodiments, the tourniquet 100 described herein exhibit less than about 2% deformation after 25% elongation when tested as such. In some embodiments, the tourniquet 100 described herein exhibit less than about 1% deformation after 25% elongation when tested as such.

According to some embodiments, the tourniquet 100 described herein exhibits less than about 8% deformation after 50% elongation when tested according to ASTM D412. In some embodiments, the tourniquet 100 described herein exhibit less than about 5% deformation after 50% elongation when tested as such. In some embodiments, the tourniquet 100 described herein exhibits less than about 2% deformation after 50% elongation when tested as such. In some embodiments, the tourniquet 100 described herein exhibits less than about 1% deformation after 50% elongation when tested as such. According to some embodiments, the tourniquet 100 described herein exhibit less than about 8% deformation after 100% elongation when tested according to ASTM D412. In a further embodiment, the tourniquet 100 exhibits about 5% deformation or less after 100% elongation when tested as such.

Advantageously, the tourniquet 100 described herein can provide enough pressure (e.g., over 100 mmHg) to occlude a vessel without requiring mechanical actuation (e.g., a buckle). Further, the tourniquet 100 can advantageously maintain pressure without the need for a locking mechanism (e.g., knot, buckle, etc.).

This ability to maintain pressure without the need for a locking mechanism can be possible because the adhesive secures overlying layers to underlying layers preventing the translational movement (slippage/sliding) of adjacent (overlying/underlying) layers. Wraps such as an elastic bandage wrap can have many overlying layers. The elastic bandage has no adhesive between these layers and is only secured at the end of the outermost wrap by a metal clip with barbs that bite into the fabric. If its clip becomes detached, all of the layers become loose and retract, causing the wrap to immediately stop providing compression.

U.S. Pat. No. 8,591,493, issued Nov. 26, 2013, describes embodiments of wound compression dressings. Some embodiments of the layers or features of the wound compression dressings described therein may have some similarities to the tourniquet 100 described herein. An important distinction between the two devices, however, is the force required for elongation. As described above, the tourniquet 100 described herein can reach 100% elongation at about 20-35 oz per inch of width. In contrast, the wound compression dressing as described in U.S. Pat. No. 8,591,493 requires about 50 pounds to achieve 100% elongation, and is thus incapable of stretching 100% when stretched with a typical amount of force (10-20 pounds). While the tourniquets described herein can reach 100% elongation at less than or equal to the typical amount of force of 10-20 pounds, the wound compression dressing of U.S. Pat. No. 8,591,493 can only reach about 20% elongation at 20 pounds. This difference in ease of stretching the two different materials can be important to the functionality of the two different materials. As described above, a traditional tourniquet can typically require about 150 mm Hg to provide proper vessel occlusion. In contrast, a compression dressing is generally designed to apply about 90 mm Hg, but no more than that as additional pressure could worsen distal bleeding via venous congestion. During application, a typical person would be able to stretch the tourniquet 100 described herein by a much greater amount when applying a typical amount of force (e.g., 20 pounds) than would be allowed by the wound compression dressings described in U.S. Pat. No. 8,591,493.

As a specific example, under 10 pounds of tension, a 100 cm long length of material described in U.S. Pat. No. 8,591,493 is stretched 20% to 120 cm and wrapped around a limb. The wrapping of the film initially results in a 10% limb compression. However, upon release of tension, the 120 cm of material retracts 12 cm and is now 108 cm (now only 8% elongated). As a result, the tension is now only 4 pounds, and the compression is only 40% of what it was initially. In contrast, under 10 pounds of tension, a 60 cm long length of tourniquet described herein is stretched 100% to 120 cm and wrapped around an identical limb. The initial wrapping of the tourniquet also results in a 10% limb compression. However, the 120 cm length of material retracts 12 cm and is now 108 cm. It was originally stretched 60 cm (100%) but is now only stretched 48 cm (still 80% stretched). As a result, the tension is 8 pounds, and the compression is still 80% of what it was initially, much higher than the film described in U.S. Pat. No. 8,591,493. Thus, the ability of the tourniquet described herein to be applied in a 100%+ elongated configuration advantageously allows the tourniquet to function to occlude vessel flow.

Thus, the ability to elongate advantageously allows the tourniquet 100 to apply greater pressure, particularly upon 3-5 wraps around the limb, that are sufficient to allow the device to function as a tourniquet.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A tourniquet comprising:
an elastic layer;
an adhesive layer on at least a portion of a first side of the elastic layer; and
a release layer on at least a portion of a second side of the elastic layer opposite from the first side thereof,
wherein the tourniquet has an elongation of over 100% when 10-25N per inch of width of tension is applied thereto.

2. The tourniquet of claim 1, wherein the elastic layer comprises polyurethane.

3. The tourniquet of claim 1, wherein the adhesive layer comprises a pressure sensitive adhesive.

4. The tourniquet of claim 1, wherein the adhesive layer is configured to retain its tack when exposed to exudates and other moisture.

5. The tourniquet of claim 1, wherein the adhesive layer comprises (meth)acrylate.

6. The tourniquet of claim 1, wherein the adhesive layer is configured to be releasable from the release layer when unwound or peeled and to remain adhered to the release layer when shear is applied thereto.

7. The tourniquet of claim 1, wherein the tourniquet is opaque.

8. The tourniquet of claim 1, further comprising a print copy layer.

9. The tourniquet of claim 1, wherein the tourniquet is configured to provide over 100 mmHg of pressure when wrapped circumferentially around a limb a plurality of times.

10. The tourniquet of claim 9, wherein the plurality comprises at least 3 times.

11. The tourniquet of claim 1, wherein a force required for 100% elongation of the tourniquet is about 40-100 oz. per inch of width.

12. The tourniquet of claim 1, wherein a force required for 100% elongation of the tourniquet is about 20-35 oz. per inch of width.

13. The tourniquet of claim 1, wherein the tourniquet is configured to reach 100% elongation at less than about 10-20 pounds.

14. The tourniquet of claim 1, wherein the elastic layer comprises an extensible material imparting recovery of at least 75% when stretched to at least 100% of its length.

15. The tourniquet of claim 1, wherein the elastic layer comprises an extensible material imparting recovery of at least 50% when stretched to at least 100% of its length.

16. The tourniquet of claim 1, wherein the tourniquet exhibits less than about 3% deformation when stretched to 25% of its length.

17. The tourniquet of claim 1, wherein the tourniquet exhibits less than about 8% deformation when stretched to 50% of its length.

18. The tourniquet of claim 1, wherein the elastic layer comprises an extensible material imparting recovery of at least 90% when stretched to at least 100% of its length.

19. The tourniquet of claim 1, wherein the tourniquet is configured to provide pressure sufficient to cause vessel occlusion when wrapped circumferentially around a limb a plurality of times without use of mechanical actuation or a locking mechanism.

20. The tourniquet of claim 1, wherein the elastic layer has a width of about 2-6 inches.

21. The tourniquet of claim 1, wherein the tourniquet is configured to apply pressure sufficient to occlude a vessel when providing less than about 200 mm Hg.

22. The tourniquet of claim 1, wherein a thickness of the elastic layer is about 50-250 microns.

23. A method for providing vessel occlusion to a patient comprising;
stretching a tourniquet comprising an elastic layer, an adhesive layer on a first side of the elastic layer, and a release layer on second side of the elastic layer, opposite the adhesive layer; and
wrapping the tourniquet around a limb of the patient a plurality of times, thereby occluding flow in the vessel.

24. The method of claim 23, wherein wrapping the tourniquet around the limb comprises aligning the tourniquet with an underlying layer.

25. The method of claim 23, wherein wrapping the tourniquet around the limb comprises adhesively securing the tourniquet to an underlying layer.

26. The method of claim 25, wherein the tourniquet is under tension while adhesively securing the tourniquet to an underlying layer.

27. The method of claim 26, wherein the tension is less than 25N per inch of width.

28. The method of claim 25, comprising stretching the tourniquet while adhesively securing the tourniquet to an underlying layer.

29. The method of claim 23, wherein stretching the tourniquet comprises stretching the tourniquet to greater than 25% of its length.

30. The method of claim 23, wherein stretching the tourniquet comprises applying less than 25 N per inch of tension to the tourniquet.

31. The method of claim 23, wherein the plurality of times comprises at least 3 times.

32. The method of claim 23, wherein wrapping the tourniquet comprises providing at least 100 mm Hg occlusive pressure to the limb.

33. The method of claim 23, wherein wrapping the tourniquet comprises providing less than about 200 mm Hg occlusive pressure to the limb, thereby occluding blood flow in a vessel of the limb.

* * * * *